US007175592B2

(12) United States Patent
Lee

(10) Patent No.: US 7,175,592 B2
(45) Date of Patent: Feb. 13, 2007

(54) MECHANICAL MASSAGE DEVICE

(75) Inventor: Shuei-Yuan Lee, Taipei (TW)

(73) Assignee: An New Industrial Co., Ltd., Taipei (TW)

( * ) Notice: Subject to any disclaimer, the term of this patent is extended or adjusted under 35 U.S.C. 154(b) by 314 days.

(21) Appl. No.: 10/860,118

(22) Filed: Jun. 4, 2004

(65) Prior Publication Data

US 2005/0272970 A1 Dec. 8, 2005

(51) Int. Cl.
*A61F 5/00* (2006.01)

(52) U.S. Cl. ........................................................ 600/38

(58) Field of Classification Search ............ 600/38–41; 601/46, 51, 50, 83, 84, 97, 101; 128/897
See application file for complete search history.

(56) References Cited

U.S. PATENT DOCUMENTS

| | | | | |
|---|---|---|---|---|
| 4,790,296 | A * | 12/1988 | Segal | 601/97 |
| 6,142,929 | A * | 11/2000 | Padgett | 600/38 |
| 6,422,993 | B1 * | 7/2002 | Hudson | 600/38 |
| 6,632,185 | B2 * | 10/2003 | Chen | 601/101 |
| 6,902,525 | B1 * | 6/2005 | Jewell | 600/38 |

OTHER PUBLICATIONS

OrgasmoTM, web.archive.org/web/20021216045137, 1 page available Dec. 16, 2002.*

* cited by examiner

*Primary Examiner*—Samuel G. Gilbert
(74) *Attorney, Agent, or Firm*—Troxell Law Office, PLLC

(57) ABSTRACT

A mechanical massage device having a pedestal, a universal coupling, a main body and an interchangeable massage piece, that is moveable in forward and backward directions and the speed and length of movement are adjustable. The massage piece also selectively rotates and vibrates.

7 Claims, 4 Drawing Sheets

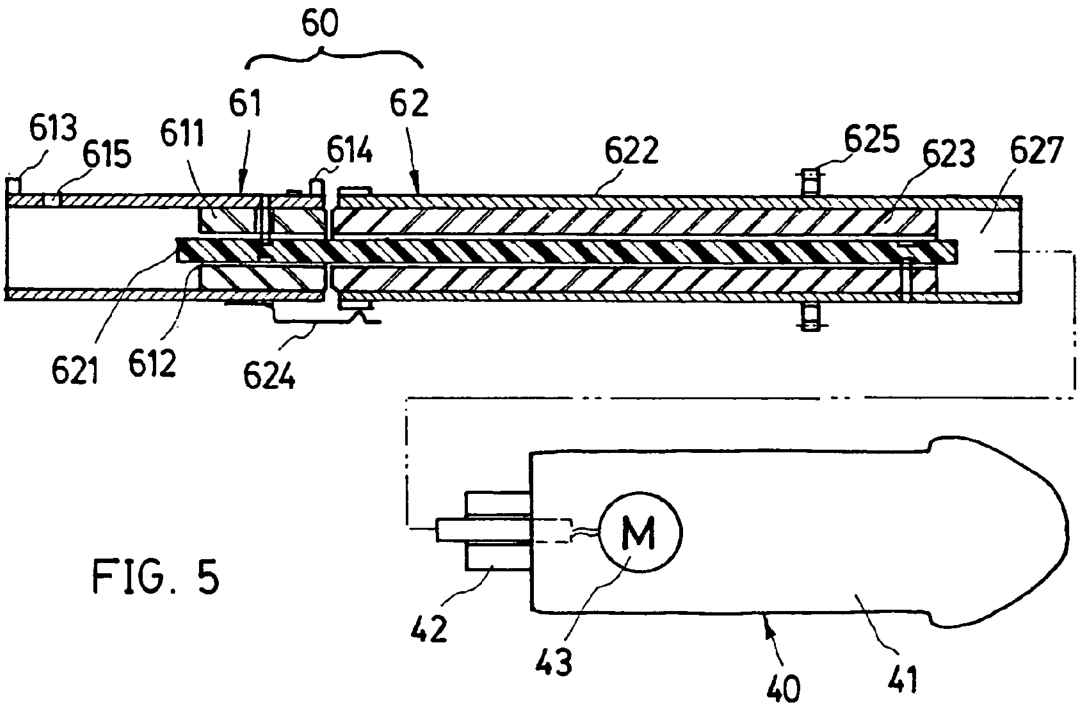
FIG. 5
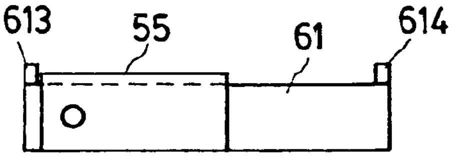
FIG. 6-A
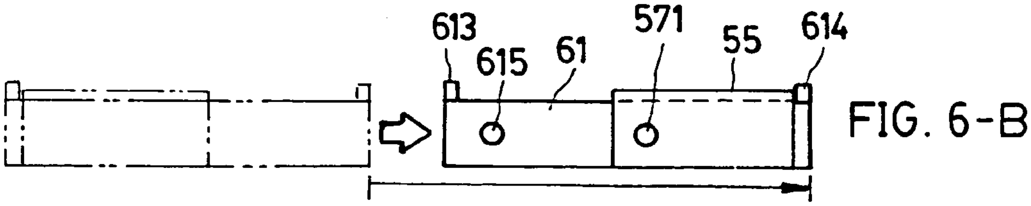
FIG. 6-B
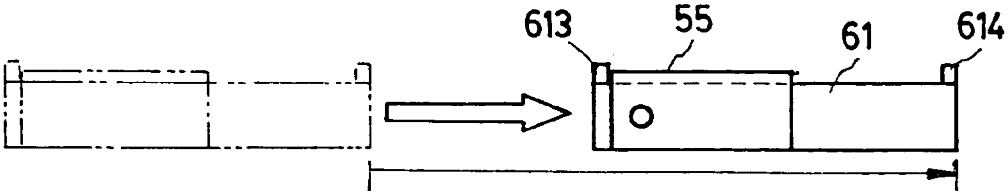
FIG. 6-C

MECHANICAL MASSAGE DEVICE

FIELD OF THE INVENTION

The present invention relates to a structure of a mechanical massage device, more particularly to an automatic massage device that is used for sexual purposes.

BACKGROUND OF THE INVENTION

The historical view of sexual concepts have been changed with new ideas. Sexual appliances are now used with wide acceptance in today's society. The present invention relates to general use mechanical massage devices, particularly to those that consist of an imitated penis (hereinafter referred to as "massage piece") with a vibrating or massaging function, and are mostly operated by hand. Others that are operated by mechanical power are rather unhandy, especially since back and forth movement limits agility and entertainment, etc., and cannot therefore satisfy the users sexual needs.

Considering the above deficiencies, the inventor focused his attention and energy to study and research to create a device that can meet users mental and physical needs with great effect where the manpower cannot be achieved.

SUMMARY OF THE INVENTION

The main object and purpose of the present invention is to provide a structure which can allow a user to easily adjust and control the movement angle of a massage piece.

The massage piece can be programmed to move back and forth in selected directions, at a selected speed and with a selected travel distance. The travel distance for the massage piece is changeable from a short to a long distance except for the general fixed movement distance.

The massage piece moving in the stated directions and the scope of back and forth movement can be adjusted to have a stronger and a weaker moving force in order to enhance the effect.

In addition to the provision of stronger movement, the massage piece can simultaneously have a rotation function, which can put the user into an orgasmic situation.

To be known by the above stated description of function, this invention aims to provide an effect of a smart mechanical structure exceeding all those known arts so far.

BRIEF DESCRIPTION OF THE DRAWINGS

FIG. 5 is a sectional view in accordance with the present invention showing a movable pole assembly.

FIG. 6-A is a diagram illustrating the first pole in a state of retracting.

FIG. 6-B is a diagram illustrating the first pole in a state of extending forward when the moving bolt is not inserted in a hole of the first pole.

FIG. 6-C is a diagram illustrating the first pole in a state of extending forward when the moving bolt is inserted in a hole of the first pole.

DETAILED DESCRIPTION OF THE PREFERRED EMBODIMENTS

Figure 1:
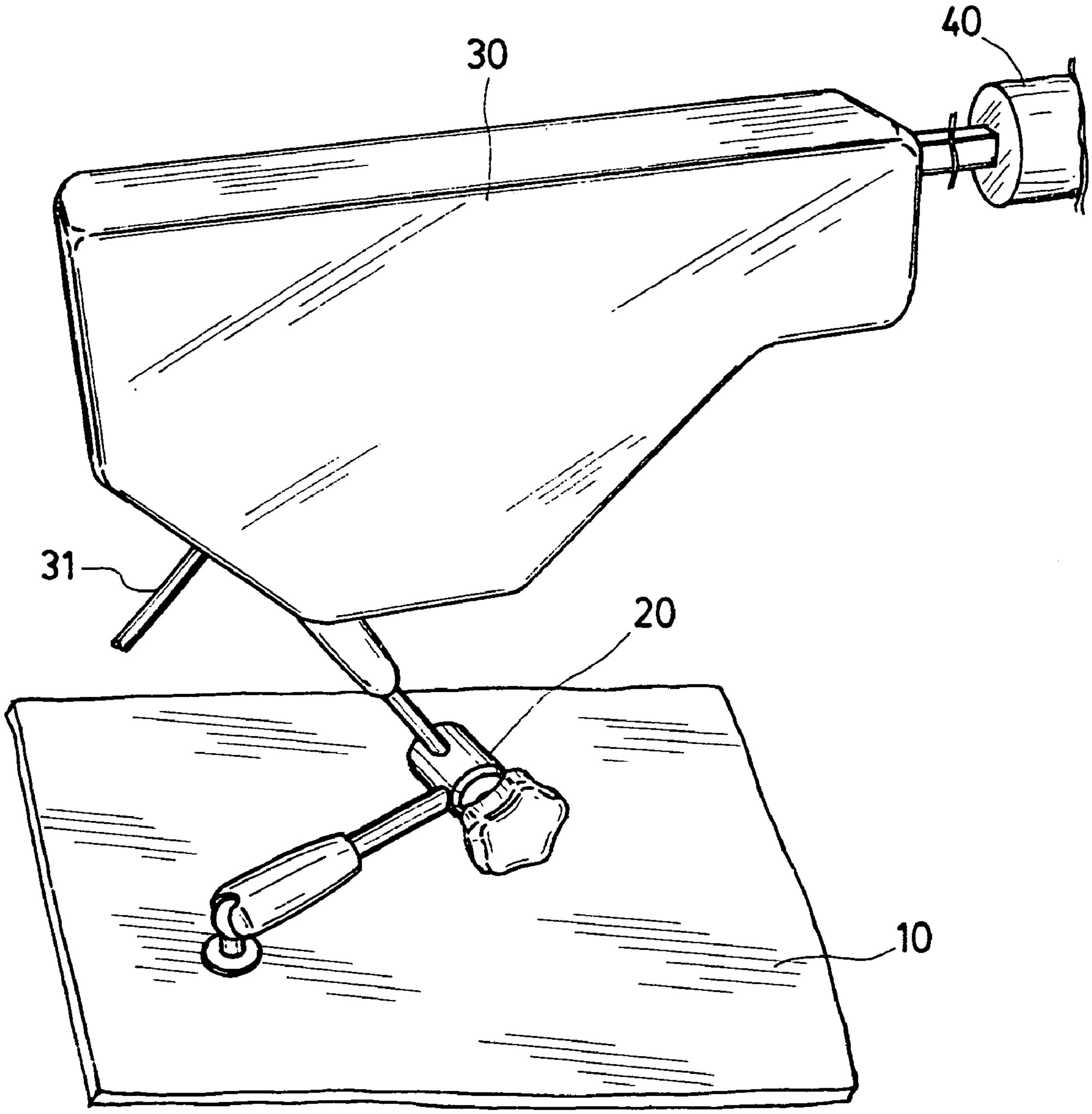
FIG. 1 is a perspective view of the present invention.

As shown in FIG. 1, the structure of this invention includes a pedestal (10), a universal coupling (20), a main body (30) and a massage piece (40).

The pedestal (10) provides stabilization when the device is sitting and being used. In addition to the universal coupling (20) fixed on a top of the pedestal (10), other coupling components that provide an adjustment function can be connected to the pedestal (10) for stabilization or to improve the user's posture.

The universal coupling (20) is placed on the pedestal (10), above which is arranged the main body (30). The universal coupling (20) is a known component by which the massage piece (40) of the main body (30) can provide users a desired variety of movements and directions.

Main body (30) provides a pre-programming action. The main body (30) includes the power cable (31) for connection to a power supply and also a relevant controlling circuit (including remote control). The relevant mechanical components are installed in an interior of the main body (30).

Figure 2:
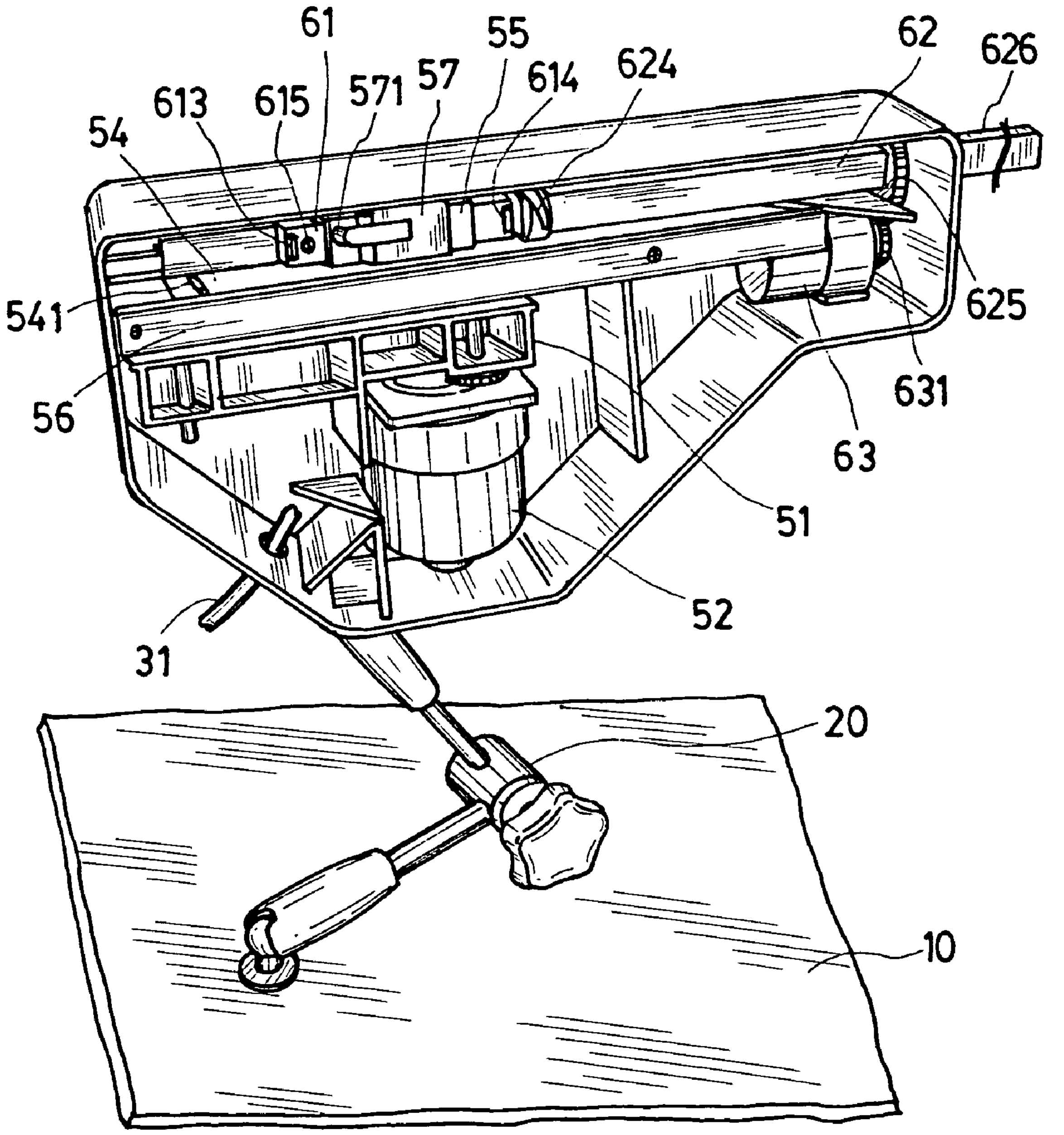
FIG. 2 is a perspective view of the present invention showing the inner structure of the main body.
Figure 3:
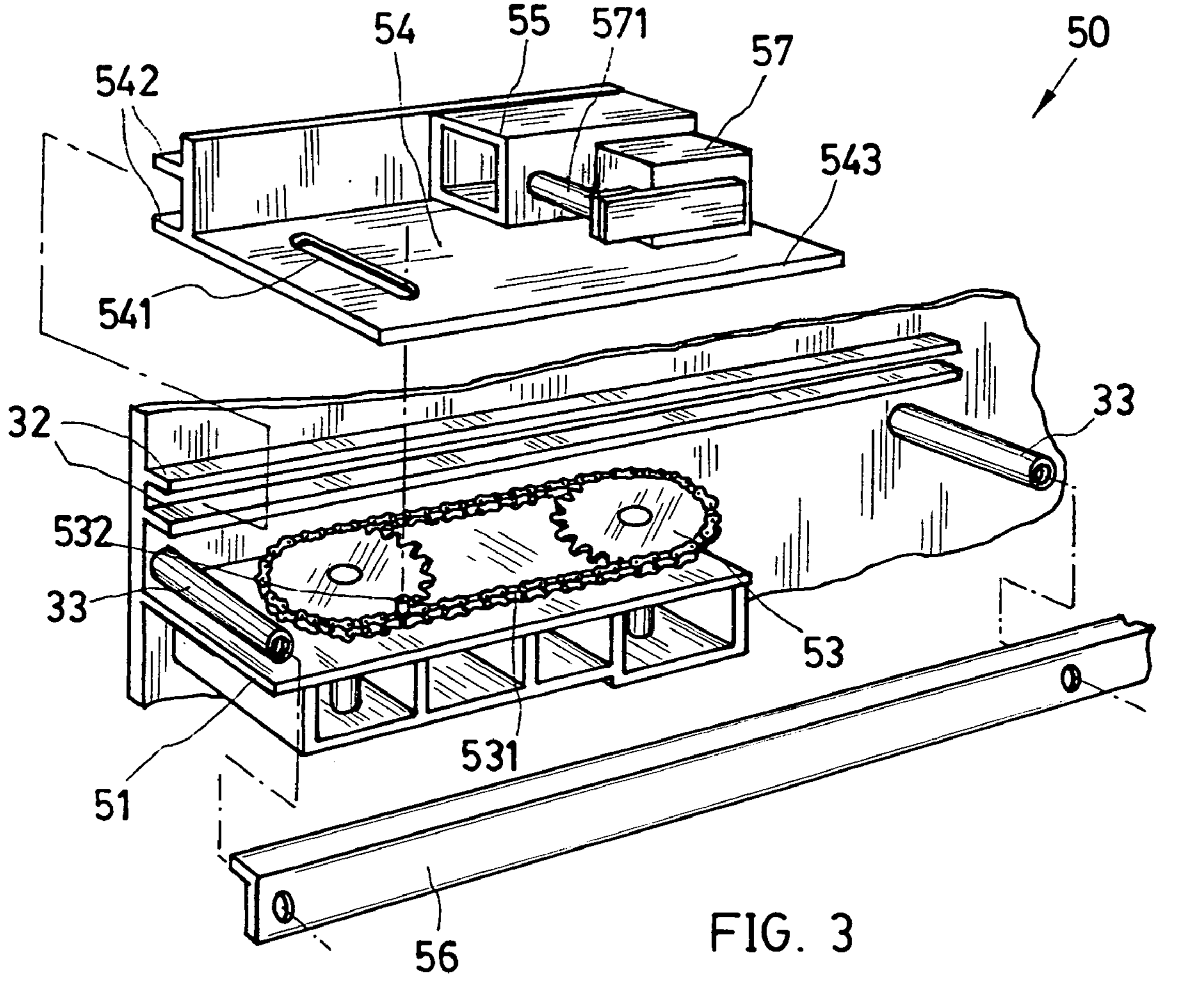
FIG. 3 is an exploded perspective view of the present invention showing a transmission chain.

As shown in FIGS. 2, 3, and 5, the mechanical components installed inside the main body (30) comprise the transmission chain assembly (50) and a movable pole assembly (60). The transmission chain assembly (50) is the component that makes the movable pole assembly (60) move reciprocally and includes a mounting seat (51), a motor (52), chain sprockets (53), a chain (531) and a slide board (54). A guiding seat (55) is located on the slide board (54).

The mounting seat (51) has a plurality of walls and is installed inside the housing of the main body (30). The motor (52), the chain sprockets (53) and the slide board (54) are mounted to the mounting seat (51) and are stable during rotation of the chain sprockets (53). The motor (52) creates a rotating power for the chain sprockets (53) that is driven by a known gear mechanism.

A movable protruding pin (532) is installed on the chain (531) and engages the slide board 54. The slide board (54) is slidably mounted above the chain sprockets (53) to move in pre-programmed back and forth directions. The movable protruding pin is inserted into a slot (541) on the slide board (54). Thus, when the chain (531) is moving, the movable protruding pin (532) moves along a oblong track defined by the chain (531), and simultaneously moves in the slot (541) so as to cause the slide board (54) to reciprocate in a straight line backward and forward in a preset direction.

Figure 4:
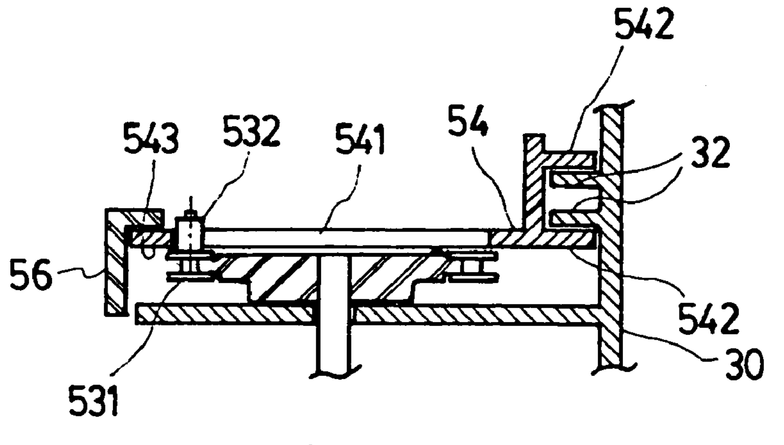
FIG. 4 is a sectional view of the present invention showing the relevant structure of a slide board.

As shown in FIGS. 3 and 4, the slide rail (542) of the slide board (54) slidably engages a slide rail (32) of the main body (30).

A baffle (56) is installed adjacent to an outside lateral edge (543) of slide board (54) and fixed on braces (33) to guide the slide board (54) between the baffle (56) and the slide rail (32).

The guiding seat (55), with a movable pole assembly (60) located in an interior thereof, is located on a top of the slide board (54). Adjacent to the guiding seat (55) is a relay (57) having a movable bolt (571) that is selectively inserted into the movable pole assembly (60) or not by passing through the guiding seat (55).

As shown in FIGS. 2, 5 and 6, the movable pole assembly comprises a first pole (61) and a second pole (62). Both the first pole (61) and the second pole (62) can have a square shape, however, there are no shape limitations on the first and second poles (61, 62). The first pole (61) is located in and has a same movement direction as the guiding seat (55).

Installed inside the first pole (61) is a fixed shank (611) having a hole (612). A shaft (621) protruding from the second pole (62) is inserted into the hole (612) of the fixed shank (611).

On an exterior of the first pole (61) are two spaced apart projecting tabs (613) and (614) between which two opposing ends of the guiding seat (55) will be slidably restricted causing a fixed moving distance. A hole (615) is located in the first pole (61) into which the movable bolt (571) is selectively moved in or out. The movable bolt (571) is controlled by the relay (57).

When the movable bolt (571) is positioned outside the hole (615), the distance of the forward movement of the first pole (61) is the moving direction of the slide board (54) reduced by the distance between the two tabs (613, 614) minus the length of the guiding seat (55) (please refer to FIGS. 6-A and 6-B). The length of the guide seat (55) is the distance between the two opposing ends. At the time when the movable bolt (571) is inserted into the hole (615), the moving forward distance of which is lengthened (please refer to FIG. 6-C).

As shown in FIG. 6-A, as soon as the guiding seat (55) is in the leftmost position, the first pole (61) is retracted backward; while the guiding seat (55) moves forward to the rightmost position, the tab (614), if the movable bolt (571) is not inserted into the hole (615), is situated against the right side of the guiding seat (55) (as shown in FIG. 6-B).

If the movable bolt (571) is inserted into the hole (615), the moving forward distance of the first pole (61) is lengthened and the guiding seat (55) moves to the rightmost position (as shown in FIG. 6-C) and the tab (614) is spaced apart from the right side of the guiding seat and the moving distance of the first pole (61) is further. The distance of the movement of the massage piece can be adjusted by selectively inserting and removing the movable bolt (571) into and out of the hole (615) by controlling the relay (57).

The second pole (62) is installed in front of the first pole (61) with the same direction and passed through the front side of the main body (30), as shown in FIGS. 1 and 2. A rotating mechanism includes the shaft (621), a pole body (622), a fixed pole (623), a conductive plate (624) and a gear (625). In a front position of the pole body (622) protruding from the main body (30) is installed a changeable massage piece (40). The shaft (621) of the rotating mechanism is installed separately inside the first pole (61) and the second pole (621), which makes both the first pole (61) and the second pole (62) move synchronously forward and backward in a straight line. When the rotating mechanism rotates the second pole (62), the synchronous back and forth movement of the first and second poles (61, 62) will not be affected.

The gear (625) is located on an exterior of the second pole (62) in an un-fixed condition and does not move longitudinally with the second pole (62) when it slides back and forth. When the gear (625) rotates, the second pole (62) will also rotate. A motor (63) has a gear (631) that rotates the gear (625) such that the running of the motor (63) drives the gear (625) via gear (631), as shown in FIG. 2, to rotate the second pole (62).

Since the shaft (621) is installed inside the first pole (61), the second pole (62) can have a rotating movement at the time of being pushed back and forth. A coupling hole (627) in front of the second pole (62) is used for the coupling of the massage piece (40).

The massage piece (40) (imitated penis) is known and may include a vibration mechanism. The present invention is to make the exterior to be designed more adaptable and applicable to the user. As shown in FIG. 5, the structure of mechanical massager (40) comprises a shell (41), a stem (42), a micro-motor and accessories (43). The shell (41) can be made of appropriate rigid materials to shape a penis or the other similar shapes. The stem (42), which provides an electrical power supply for the micro-motor (43) is installed into the coupling hole (627) and can vibrate the massage piece (40) by rotating an associated cam (not shown).

To summarize, the present invention is to provide an integrated movement that can be controlled under an integrated electric circuit, such that a button or remote control of the motor (52) can control the speed of movement. The controlling relay (57) can vary the range of movement and motor (63) can also make the massage piece (40) rotate. The vibration can be provided by the motor (43). It is the electric circuit design that naturally makes the performance of multi-movements possible and further enhances the entertainment and effect of the device.

The disclosed embodiment is only one of the best performances. Any minor changes or modifications partially or wholly to the present invention conducted by other professionals and made publically known or familiar shall be deemed to be derived from the present inventive concept and will still fall within the scope of claims of the present invention.

What is claimed is:

1. A mechanical massage device comprising:

a) a pedestal;

b) a main body located above the main body and having:

i) a movable pole assembly slidably located in the main body and having a first end protruding from the main body wherein the pole assembly includes a first pole rotatably connected to a second pole; and ii) a sliding device connected to the movable pole assembly and controlling a forward and backward movement of the movable pole assembly relative to the main body; and c) a massage piece removably connected to the first end of the movable pole assembly, wherein the sliding device includes:

a) a slide board having a slot and slidably located within the main body;

b) a chain having a movable protruding pin inserted into the slot; and c) a slide motor controlling and driving the chain, such that movement of the movable protruding pin causes the slide board to reciprocate relative to the main body.

2. The mechanical massage device according to claim 1, wherein the movable pole assembly includes a side cole, the slide board includes:

a) a guiding seat having a guiding seat hole with the pole assembly slidably inserted into the guiding seat; and b) relay having a movable bolt movable between an engaged position in which the movable bolt is inserted into the guiding seat hold and the side hole, and a disengaged position in which the movable bolt is retracted from the guiding seat hold and the side hole.

3. The mechanical massage device according to claim 1, further comprising an adjustable coupling located between the pedestal and the main body.

4. A mechanical massage device comprising:

a) pedestal;

b) a main body located above the main body and having:

i) a movable pole assembly slidably located in the main body and having a first end protruding from the main body wherein the pole assembly includes a first pole rotatably connected to a second pole; and ii) a sliding device connected to the movable pole assembly and controlling a forward and backward movement of the movable pole assembly relative to the main body; and c) a massage piece removably connected to the first end of the movable pole assembly, further comprising a rotation device having:

a) a first gear located on an exterior of the second pole of the movable pole assembly such that rotation of the first gear causes rotation of the second pole relative to the first pole, and such that first gear does not reciprocate with the forward and backward movement of the movable pole assembly; and b) a rotation motor having a second gear engaging the first gear, such that the rotation motor rotates the first gear.

5. The mechanical massage device according to claim 4, further comprising an adjustable coupling located between the pedestal and the main body.

6. A mechanical massage device comprising:

a) a pedestal;

b) a main body located above the main body and having:

i) a movable pole assembly slidably located in the main body and having a first end protruding from the main body wherein the pole assembly includes a first pole rotatably connected to a second pole; and ii) a sliding device connected to the movable pole assembly and controlling a forward and backward movement of the movable pole assembly relative to the main body; and c) a massage piece removably connected to the first end of the movable pole assembly, wherein the massage piece includes a vibration device and is electrically connected to the movable pole assembly.

7. The mechanical massage device according to claim 6, further comprising an adjustable coupling located between the pedestal and the main body.

* * * * *